United States Patent [19]

Yang et al.

[11] Patent Number: 4,826,873

[45] Date of Patent: May 2, 1989

[54] 2,3-DIHYDROXY-3-PHENYL-N-(2-PHENYL-ETHYL)-PROPIONIC ACID AMIDES DERIVATIVES THEREOF

[75] Inventors: Ming-he Yang; Yan-rong Chen; Geng-tao Liu; Liang Huang, all of Beijing, China

[73] Assignees: Chinese Academy of Medical Sciences, Beijing, China; Bayer Aktiengesellschaft, Leverkusen, Fed. Rep. of Germany

[21] Appl. No.: 4,360

[22] Filed: Jan. 15, 1987

[30] Foreign Application Priority Data

Jan. 20, 1986 [GB] United Kingdom ............... 8601258

[51] Int. Cl.⁴ .................. A61K 3/165; C07C 69/16; C07C 103/26; C07D 317/12
[52] U.S. Cl. ..................... 514/467; 514/547; 514/548; 514/622; 514/893; 514/894; 549/450; 560/105; 564/170
[58] Field of Search ....... 564/170; 560/105; 549/450; 514/467, 547, 548, 622, 893, 894

[56] References Cited

U.S. PATENT DOCUMENTS

| | | | |
|---|---|---|---|
| 2,320,497 | 6/1943 | Wenner | 564/170 |
| 2,721,214 | 10/1955 | Troutman | 564/170 X |
| 2,812,363 | 11/1957 | Mills | 564/170 X |
| 4,341,718 | 7/1982 | Kim et al. | 564/170 X |
| 4,518,789 | 5/1985 | Yu et al. | 560/105 |

FOREIGN PATENT DOCUMENTS 711018 6/1954 United Kingdom ............... 564/170

1171670 10/1968 United Kingdom ............... 564/170

OTHER PUBLICATIONS

Prakash et al, Indian J. Chem., vol. 19B, pp. 1075 to 1076 (1980).

*Primary Examiner*—Floyd D. Higel
*Attorney, Agent, or Firm*—Sprung Horn Kramer & Woods

[57] ABSTRACT

Compounds of the general formula

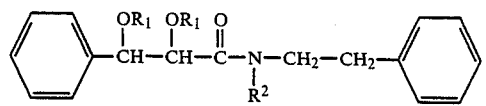

wherein
$R_1$ represents hydrogen, an acyl group having 1 to 18 carbon atoms or both $R_1$ together the group

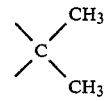

$R_2$ represents hydrogen or a methyl group, have been isolated in small amounts from the leaves of *Clausena lansium*. The new compounds are to be used for the production of compositions for the use of the treatment of acute and chronical viral hepatitis, liver intoxication, hypoxia or amnesia.

10 Claims, No Drawings

2,3-DIHYDROXY-3-PHENYL-N-(2-PHENYL-ETHYL)-PROPIONIC ACID AMIDES DERIVATIVES THEREOF

The present invention relates to new amides, their isolation from plants of the Rutaceae Clausena species, certain derivatives thereof and their use as hypoxiaprotective and antiamnestic agents. The invention is also concerned with pharmaceutical compositions containing said amides or its derivatives with their manufacture.

*Rutaceae Clausena anicata* was reported to be used as a folk medicine in certain parts of Africa (I. Mester et al., Planta Medica 32 (1) 81, 1977). It has also been reported that the crude extract of *Clausena indica* Oliv. has cardiovascular activity and that two coumarin derivatives, Clausmarins A and B, isolated (TDC) from *Clausena pentaphylla* (Roxb.) showed spasmolytic activity in animal test (Dhan Praktash et al., Phytochem. 17, 1194, 1978; Aboo Shoeb et al., J.C.S. Chem. Commun. 281, 1978). About fifty constituents have already been isolated from the roots, stems, etc. of various species of Clausena. Most of these constituents are derivatives of coumarin, carbazole and terpene; so far only two linear carboxylic acid amides were reported to be present in the leaves of Clausena plants (S. R. Johns et al., Aust. J. Chem. 20, 2795, 1967; Dhan Prakash et al., Indian J. Chem. Sect. B 19B (12), 1075, 1980).

It has now been found that the leaves of *Clausena lansium* contain new amides.

The present invention is directed to compounds of the general formula (I):

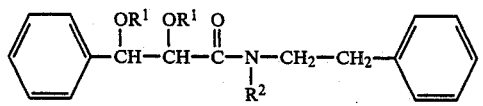

wherein $R^1$ represents hydrogen, an acyl group having 1-18 carbon atoms or both radicals $R^1$ together form the group and

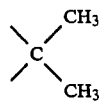

$R^2$ represents hydrogen or a methyl group.

Preferred compounds according to general formula (I) are those wherein $R^1$ represents hydrogen or an acyl group having 1 to 4 carbon atoms and $R^2$ represents hydrogen or methyl.

Especially preferred are those compounds wherein $R^1$ represents hydrogen or the acetyl group.

The compound I, $R^1=H$, $R^2=CH_3$ apparently is a mixture of isomers arising from the differences in the relative position of the two hydroxyl groups (cis or trans). The present invention is also directed to the isolation of the compound I, $R^1=H$, $R^2=CH_3$ which comprises the steps of:

(a) treating leaves of *Clausena lansium* with boiling water, (b) adding dilute acid (e.g. HCl) to the concentrated aqueous extract, (c) passing the supernatant through a column of cation ion exchange resin, preferably in its $H^+$-form, (d) treating the resin with a base, preferably aqueous ammonia, (e) extracting the resin with an organic solvent such as ethers, chloroform, methylene chloride, acetic acid esters of $C_1-C_6$ alcohols or $C_2-C_6$ ketones, preferably with diethyl ether, (f) chromatographing the concentrated extract on silica or aluminum oxide column with chloroform, methylene chloride, ether or a chloroform/methanol mixture as eluting agent and (g) collecting and concentrating the eluate with an Rf-value of 0.37 on TLC (silica gel plate, $CHCl_3:MeOH=91:3$ as eluting agent).

It is preferred to recrystallize the crude products obtained by the above isolation methods from alcohols, e.g. methanol or ethanol.

Derivatives of the compound according to the general formula (I), wherein $R^1$ represents hydrogen may be synthesized by acylation and ketalization methods known per se.

The present invention also relates to pharmaceutical compositions and medicaments containing compounds of formula (I) as an active ingredient and to the manufacture of these compositions.

The invention is also directed to the use of compounds of formula (I) as hepatoprotective agents against chemical toxins and for increasing the detoxification function of the liver.

The acute toxicity of the compounds of the formula (I) was found to be very low.

When tested for hepatoprotection action the compounds according to the invention decreased the elevated serum transaminase (SGPT) of mice intoxicated with $CCl_4$.

The pharmaceutical compositions according to the invention may for example take the form of ointments, gels, pastes, creams, sprays (including aerosols), lotions, suspensions, solutions and emulsions of the active ingredient in aqueous or non-aqueous diluents, syrups, granules or powders.

The compositions are preferably in the form of a sterile isotonic aqueous solution or in the form of tablets, capsules, pills and suppositories comprising a compound of the invention either alone or in admixture with a diluent.

The diluents to be used in pharmaceutical compositions (e.g. granules) adapted to be formed into tablets, degrees, capsules and pills include the following:

(a) fillers, e.g. starch, sugars, and silicic acid; binding agents, e.g. cellulose derivatives, alginates, gelatine and polyvinyl pyrrolidone;

(c) moisturizing agents, e.g. glycerol;

(d) disintegrating agents, e.g. agar-agar, calcium carbonate and sodium bicarbonate;

(e) resorption accelerators, e.g. quarternary ammonium compounds;

(f) surface active agents, e.g. cetyl alcohol;

(g) adsorptive carriers, e.g. kaolin and bentonite;

(h) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The production of the above-mentioned pharmaceutical compositions and medicaments is carried out by any method known in the art, for example by mixing the active ingredient(s) with the diluents(s) to form a pharmaceutical composition (e.g. a granulate) and then forming the composition into the medicament (e.g. tablets).

The pharmaceutical compositions according to the invention preferably contain about 0.1 to 99.5, more preferably from about 0.5 to 95% of the active ingredient by weight of the total composition.

The preferred daily dose for administration of the medicaments of the invention is 0.001 mg to 0.2 mg of the active ingredient.

The following Examples illustrate the invention.

EXAMPLE 1

Isolation of 2,3-dihydroxy-N-methyl-3-phenyl-N-(2-phenylethyl)-propionic acid amide of the formula

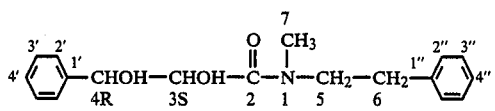

80 kg of dried leaves of *Clausena lansium* (Lour) Skeels were boiled with water. The aqueous extract was concentrated to give 18 kg of crude syrup. 16 kg of the crude syrup were treated with 0.06N HCl (80 l) and the supernatant was passed through a column of wet $H^+$-form cation ion exchange resin (from 48 kg of $Na^+$-form cation ion exchange resin). The resin was then washed with deionized water, treated with 2% aqueous $NH_4OH$ (32.2 l) and finally extracted with diethyl ether (60 l) and finally extracted with diethyl ether (60 l). The concentrated ether extract as a syrup was chromatographed repeatedly on silica gel columns containing 20-100 times of its weight with chloroform as eluting agent. The conc. chloroform eluate with $R_f$=0.37 on the TLC was collected and concentrated. The crystals thus obtained were recrystallized from methanol. 11.18 g of white needles, m.p. 145° to 147° C. were obtained. $[\alpha]_D^{22}$-65.8° C. (0.19 in $CHCl_3$).

Elementary analysis:

|   | calculated for $C_{18}H_{21}NO_3$ | found |
|---|---|---|
| C % | 72.24 | 71.94 |
| H % | 7.08 | 7.10 |
| N % | 4.68 | 4.46 |

High resolution-MS $M^+$=299.1483.

IR $\gamma_{max}^{KBr}$ cm$^{-1}$: 3280 (OH), 3080, 3060, 3020, 1580, 1490, 750, 690 (monosubstituted benzene), 1620 (amide carbonyl).

UV $\lambda_{max}^{MeOH}$ nm (log ε): 257 (2.80).

H$^1$-NMR (in $CDCl_3$); chemical shift and assignment:

| δ ppm (J, Hz) | hydrogen |
|---|---|
| 2.70 + 2.90 (s; s; 3H) | N—CH$_3$ |
| 2.78 (t; J=6; 2H) | C$_6$—H |
| 3.42 (s; 2H, disappeared on addition of D$_2$O) | OH |
| 3.51 (m; 2H) | C$_5$—H |
| 4.35 + 4.56 (d; d; J=5; 1H) | C$_3$—H or C$_4$—H |
| 4.85 (d; J=5; 1H) | C$_3$—H or C$_4$—H |
| 7.00-7.40 (m; 10H) | aromatic H |

$^{13}$C-NMR in $CDCl_3$; chemical shift and assignment:

| carbon | ppm |
|---|---|
| 2 | 173.5 |
| 3 | 76.3 |
| 4 | 73.2 |
| 5 | 51.1 + 52.0 |
| 7 | 34.3 + 35.6 |
| 6 | 36.0 + 36.5 |
| 1' | 144.3 |
| 1'' | 140.0 + 140.3 |
| the rest ten aromatic carbons | 127.1 |
|  | \| |
|  | 130.3 |

The compound reacted with $HIO_4$ to give benzaldehyde which was identified by its 2,4-dinitrophenylhydrazone.

Acetylation

The compound was acetylated with acetic anhydride in pyridine to give an amorphous acetate.

Elementary analysis:

|   | Calculated for $C_{22}H_{25}NO_{35}$ | found |
|---|---|---|
| C % | 68.93 | 68.69 |
| H % | 6.53 | 6.40 |
| N % | 3.66 | 3.95 |

IR, $\nu_{max}^{film}$ cm$^{-1}$: 1740(ester C=O), 1655(amide C=O, 1210(C—O).

MS, m/z(%): 383(M$^+$, 5), 292(M$^+$-91, 18), 249(292-43, 31), 207(249-43, 25).

$^1$H-NMR in $CDCl_3$ chemical shift and assignment:

| δ ppm (J, Hz) | H |
|---|---|
| 1.93 (two s, 3H) 1.95 | CH$_3$COO— |
| 2.03 (s, 3H) | CH$_3$,COO— |
| 2.95 (two s, 3H) 3.06 | CH$_3$N— |
| 2.84 (two t, J=7, 2H) 3.01 | C$_6$—H |
| 3.63 (two t, J=7, 2H) 3.71 | C$_5$—H |
| 5.62 (two d, J=8, 1H) 5.72 | C$_3$—H |
| 6.07 (d, J=8, 1H) | C$_4$—H |
| 7.2-7.5 (m, 10H) | aromatic H |

Ketalization

The compound I, R=H was treated with acetone using hyperchloric acid as catalyst in room temperature to give crystals.

IR, $\gamma_{max}^{film}$ cm$^{-1}$: 1665(amide C=O).

MS, m/z(%): 339(M$^+$, 5), 281(10), 190(28), 177(30), 162(32), 119(100), 105(74), 91(64), 77(25).

$^1$H-NMR in CDCl$_3$ chemical shift and assignment:

| δ ppm (J, Hz) | H |
|---|---|
| 1.46 (two s, 3H) 1.52 | CH$_3$—C |
| 1.80 (two s, 3H) 1.85 | CH$_3$—C |
| 2.31 (two m, 2H) 2.65 | C$_6$—H |
| 2.51 (s, 3H) | CH$_3$—N |
| 3.15 (m, 2H) | C$_5$—H |
| 4.99 (two d, J=7, 1H) 5.20 | C$_3$—H |
| 5.36 (two d, J=7, 1H) 5.43 | C$_4$—H |
| 7.00 \| (m, 10H) 7.52 | aromatic H |

EXAMPLE 2

Influence of the compound of the general formula I, R$_1$=H, R$_2$=CH$_3$, on liver functions Male Kunming strain mice weighing 18–22 grams were used throughout the experiments. The compound to be tested was suspended in 5% Tween 80 and given orally by gavage. The vehicle of 5% Tween 80 solution was administered to control mice via the same route. In the vitro experiments, the compound was dissolved in dimethylformamide and added directly into the incubation mixture.

The parameters adopted for hepatotoxicicity included serum tranaminase (SGPT), liver triglycerides, and pathological examination of liver tissues. The liver lesions were scored mainly by the extent of inflammation and necrosis and graded from 0 to 4.

1. Hepatoprotective action.
1.1. Effect of the compound isolated from LCL on SGPT level of CCl$_4$-intoxicated mice.

Mice were divided into several groups.

The control group received the vehicle. The other groups were given two doses of the compound (250 mg/kg) at an interval of 8 h, respectively. All the mice were injected ip 10 ml/kg of 0.1% CCl$_4$ in vegetable oil 24 h after the last administration of the compound. The mice were fasted for 16 h and sacrificed by decapitation. SGPT and liver lipids were determined. A piece of liver was processed into sectins for pathological examination.

As shown in table 1, the compound significantly decreased the elevated SGPT of mice intoxicated with CCl$_4$. 1.2 Protective action of the compound against CCl$_4$, acetaminophen and thioacetamide in mice.

In the experiments of anti-CCl$_4$ hepatotoxicity, mice were first injected 10 ml/kg of 0.15% CCl$_4$ in vegetable oil every other day for three doses. The treatment of mice with the compound (250 mg/kg daily) started from the second to fifth day after the first injection of CCl$_4$. The determination of SGPT and pathological examination of liver tissues were performed on day 7 of the experiment. The results indicate that the compound exhibited significant SGPT lowering action but had no effect on liver lesions (Table 2).

In another experiment, mice were first administered two doses of the compound and injected ip 10 ml/kg of 0.1% CCl$_4$ in vegetable oil 24 h after administration of the second dose. As shown in table 3, 250 mg/kg of the compound was effective for decreasing SGPT level and liver injuries, while 125 mg/kg was without effect.

In the experiment of thioacetamide hepatotoxicity, mice were treated according to the procedure of CCl$_4$ intoxication as described above except that thioacetamide 50 mg/kg was injected instead of CCl$_4$. The results showed that the compound markedly lowered the SGPT levels (table 4).

In the anti-acetaminophen hepatotoxicity experiment, mice received two doses (250 mg/kg) of the compound on the first day and the same dose on the second day. A dose of 150 mg/kg of acetaminophen was injected ip 6 h after the last dose of the compound, SGPT was determined and liver tissues were examined 20 h after acetaminophen injection. The compound was shown to be inactive.

1.3 Effect of the compound on serum and liver transaminase (GPT) levels of normal mice.

Groups of mice were administered the vehicle or 250 mg/kg of the compound once daily for 7 consecutive days. The serum and liver GPT were determined 24 h after the last dose administration. As shown in table 5, SGPT level of the mice treated with compound was slightly higher than that of the control but the difference was not significant. Similar results were obtained for liver GPT.

2. Mechanism of the protective action of the compound against CCl$_4$ hepatotoxicity.

CCl$_4$ hepatotoxicity has been considered to be due to formation of free radicals which initiate lipid peroxidation or covalent binding to macromolecules of microsomes. Thus, the structures and function of cell membranes were destroyed. The effect of the compound on CCl$_4$ induced lipid peroxidation (malonic dialdehyde, MDA, in vitro, and diene conjugates in vivo) and $^{14}$CCl$_4$ covalent binding to lipids and proteins of microsomes were investigated.

Lipid peroxidation:

MDA formation: The compound was pre-incubated with NADPH-reduced liver microsomes from phenobarbital-induced mice at 37° C. for 15 minutes, 10 ul of CCl$_4$ (diluted with 20 volume of ethanol) was added into the incubation mixture, reincubated for 20 minutes. The production of MDA was determined by the method of thiobarbituric acid. The results indicate that 1 mM of the compound inhibited MDA production initiated by CCl$_4$ in vitro.

Diene conjugates: Mice were given two doses of 250 mg/kg of the compound on the first day and followed by the same dose on the second day and then received an injection of 1 ml/kg of CCl$_4$. The mice were killed 1 h after the CCl$_4$ injection. The diene conjugates in liver microsomes were extracted with chloroform-methanol (2:1) and washed with methanol 0.9% NaCl solution. The absorption of diene conjugates in the chloroform layer at 243 nm was measured with spectrophotometer. It was found that the compound would not inhibit diene conjugates production in livers from CCl$_4$-intoxicated mice (table 6).

$^{14}$CCl$_4$ covalent binding:

The condition of incubation was similar to that of MDA production. The compound was pre-incubated with NADPH-reduced liver microsomes for 10 minutes. The final concentration of the compound was 1 mM. $^{14}$CCl$_4$ 0.5 uci was added to the incubation mixture. Incubation was continued for another 60 minutes. The radio-activity of $^{14}$CCl$_4$ in microsomal lipids and proteins was separated by the method of extraction of diene conjugates and counted by liquid scintillation.

The results indicated that the covalent binding of $^{14}CCl_4$ to microsomal lipids and proteins was not inhibited by the compound.

3. Induction of hepatic microsomal cytochrome P-450.

The liver microsomal cytochrome P-450 plays a key role in the detoxification of xenobiotics. Since the compound was shown to be able to decrease hepatotoxicity induced by chemicals in mice, it is of interest to study the effect of the compound on cytochrome P-450. Mice were administered 250 mg/kg of the compound once daily for 3 days. The control mice received the vehicle. The mice were killed after fasting overnight. Liver microsomes were prepared and microsomal monooxygenases were determined.

The data are shown in table 7, the hepatic cytochrome P-450, cytochrome $b_5$, NADPH-cytochrome c reductase, aminopyrine demethylase and benzo(a)pyrene hydroxylase activities were all increased significantly by the compound. The increase of liver size and microsomal protein content were not seen in the compound treated mice.

In another experiment, mice were given a dose of 250 mg/kg of the compound. Sodium pentobarbital (50 mg/kg) was injected ip 1 and 24 h after administration of the compound. The sleeping time was estimated by recording the interval of disappearance and recovery of righting reflex. The data are listed in table 8. The sleeping time of mice was shortened significantly by administration of the compound, 24 h before the injection of pentobarbital, the sleeping time of mice was prolonged markedly instead of being shortened when the compound was given 1 h prior to pentobarbital injection. However, prior administration of the compound did not affect sleeping time of mice injected with barbital which is not metabolized by the liver. It means that the prolongation of pentobarbital sleeping time by the compound was due to the inhibition of liver drug metabolism enzyme. Therefore, the compound has biphasic actions on the hepatic microsomal cytochrome p-450, i.e. inhibition followed by induction.

In conclusion, the compound of the general formula (I), $R_1=H$, $R_2=CH_3$ has hepatoprotective action against $CCl_4$. The results of further investigations on the compound indicated that it also protected against thioacetamide hepatotoxicity, and that it could inhibit lipid peroxidation of microsmomes induced by $CCl_4$. In addition, the compound ohas inducing action on hepatic cytochrome p-450.

TABLE 1

Effect of the compound of the general formula (I), $R_1=H$, $R_2=CH_3$ (250 mg/kg × 2) isolated from the leaves of Clausena lansium (Lour) Skeels on SGPT levels of $CCl_4$ intoxicated mice (9 per group)

| Constituents | SGPT unit % X ± SE | P |
|---|---|---|
| Control | 1678 ± 261 | |
| Compound (250 mg/kg × 2) | 727 ± 266 | <0.05 |

TABLE 2

Therapeutic effect of the compound on $CCl_4$ (0.15% in vegetable oil 10 ml/kg/day × 3, PO) hepatotoxicity in mice (8 per group).

| Group | SGPT unit % x ± SE | P |
|---|---|---|
| Control | 2695 ± 110 | |
| Compound | 1801 ± 312 | <0.01 |
| (250 mg/kg/day × 4) | | |

TABLE 3

Protective action of the compound against $CCl_4$ (0.1% 10 ml/kg, i.p) hepatotoxicity in mice

| | Control | Compound 125 mg/kg | 250 mg/kg |
|---|---|---|---|
| SGPT unit % | 3016 ± 23 | 2727 ± 162 | 2270 ± 221 |
| Liver lipids mg/g | 21.0 ± 4.2 | 21.0 ± 3.8 | 22.5 ± 5.5 |
| Liver lesions | | | |
| Inflammation (Grade) | 1.70 | — | 0.16 |
| Necrosis (Grade) | 2.33 | — | 0.72 |

Nine mice per group. ± SE.
<0.01

TABLE 4

Protective action of the compound against thioacetamide (50 mg/kg, ip) hepatotoxicity in mice

| Group | SGPT unit % ± SE | Liver lipids mg/g ± SE |
|---|---|---|
| Control | 1696 ± 231 | 61 ± 11.7 |
| Compound (250 mg/kg × 2) | 1045 ± 166 | 59 ± 11.3 |

Nine per group.
<0.05.

TABLE 5

Effect of the compound on serum and liver transaminase (GPT) level of normal mice (8 per group)

| Group | SGPT unit % ± SE | LGPT unit % ± SE |
|---|---|---|
| Control | 217 ± 17.5 | 260 ± 11.6 |
| Compound (250 mg/kg/day × 7) | 272 ± 27.8 | 234 ± 13.6 |

TABLE 6

Effect of the compound on $CCl_4$—initiated lipid peroxidation of liver microsomes (MDA in vitro and diene conjugates in vivo)

| | Control | Compound |
|---|---|---|
| MDA OD × 100/1.5 mg | 35.5 ± (3) | 29.7 ± 4(3) |
| Inhibition % | | 16.3 |
| Diene conjugates OD × 100/g liver | 55.8 ± 2.3(8) | 54.8 ± 3.3(8) |
| Inhibition % | | |

Figures in the parenthesis are number of the determinations.

TABLE 7

Induction of hepatic microsomal cytochrome P-450 by the compound in mice (6 per group)

| | Control | Compound 250 mg/kg day × 3 | P |
|---|---|---|---|
| Liver weight g % | 4.0 ± 0.2 | 4.3 ± 0.2 | >0.05 |
| Microsomal protein mg/g liver | 6.3 ± 0.3 | 7.0 ± 0.5 | >0.05 |
| Cytochrome P-450 nmol/mg protein | 0.87 ± 0.07 | 1.23 ± 0.06 | <0.01 |
| NADPH—cytochrome | 103 ± 2.5 | 148 ± 2.5 | <0.01 |

TABLE 7-continued

Induction of hepatic microsomal cytochrome P-450 by the compound in mice (6 per group)

| | Control | Compound 250 mg/kg day × 3 | P |
|---|---|---|---|
| C reductase, nmol cytochrome c reduced/min/mg protein | | | |
| Cytochrome $b_5$ nmol/mg protein | 0.15 ± 0.01 | 0.16 ± 0.016 | >0.05 |
| Aminopyrine demethylase, nmol HCHO/min/mg protein | 81 ± 63 | 107 ± 5.8 | <0.01 |
| AHH nmol/min/mg protein | 2.6 ± 0.4 | 6.2 ± 0.42 | <0.01 |

TABLE 8

Effect of the compound on barbiturates sleeping time in mice (10 per group)

| Barbiturate | Group | Interval between compound and barbiturate | Sleeping time X ± SE | P |
|---|---|---|---|---|
| Pentobarbital 50 mg/kg | Control | | 71 ± 7 | |
| | Compound | 1 h | 132 ± 13 | <0.01 |
| | Compound | 24 h | 45 ± 6 | <0.01 |
| Barbital 200 mg/kg | Control | | 197 ± 27 | |
| | Compound | 1 h | 172 ± 13 | >0.05 |

EXAMPLE 3

Isolation of the compound of the formula (so-called compound 7)

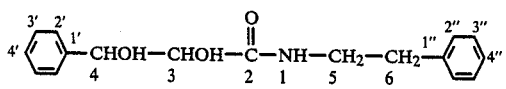

80 kg of dried leaves of Clausena lansium (Lour) Sdeels were boiled with water. The aqueous extract was concentrated to give 18 kg of crude syrup. 16 kg of the crude syrup were treated with 0.06N HCl (80 l) and the supernatant was passed through a column of wet H+-form cation ion exchange resin (from 48 kg of Na+-form cation ion exchange resin). The resin was then washed with deionized water, treated with 2% aqueous NH$_4$OH (32.2 l) and finally extracted with diethyl ether (60 l). The concentrated ether extract was treated repeatedly on silica gel columns (ratio varied from 100:1 to 2:1) with chloroform as eluting agent. The concentrated chloroform eluate with Rf=0.28 on TLC was collected and concentrated. The crystals thus obtained were recrystallized from methanol. 0.3 g of white prism crystals, m.p. 151°-152° C. were obtained $[\alpha]_D^{28}+38°$ (0.30 in MeOH).

Elementary analysis:

| | Calculated for $C_{17}H_{19}NO_3$ | found |
|---|---|---|
| C % | 71.58 | 71.86 |
| H % | 6.67 | 6.47 |
| N % | 4.91 | 4.68 |

High resolution -MS M+ =285.1395.

IR $\gamma_{max}^{KBr}$ cm$^{-1}$: 3300 (OH), 3190, 1570(N—H), 1655(amid C=O) 3060, 3030, 1605, 1495, 760, 700 (monosubstituted benzene).

UV $\lambda_{max}^{MeOH}$ nm (log ε): 255 (2.60).

MS m/z(%); 285(M+, 1), 267(M—H$_2$O, 0.3), 179(45), 148(6), 120(6), 105(100), 91(48), 77(64).

$^1$H-NMR (in CDCl$_3$); chemical shift and assignment:

| δ ppm (J, Hz) | hydrogen |
|---|---|
| 2.95(m, 2H) | C$_6$—H |
| 3.25(m, 2H) | C$_5$—H |
| 4.05(t, J=4, 1H) | C$_3$—H |
| 4.82(t, J=4, 1H) | C$_4$—H |
| 5.45(d, J=4, 1H, disappeared on addition of D$_2$O) | OH |
| 5.55(d, J=4, 1H, disappeared on addition of D$_2$O) | OH |
| 7.02-7.39(m, 10H) | aromatic H |
| 7.44(br, 1H) | N—H |

$^{13}$C-NMR in CDCl$_3$; chemical shift and assignment:

| carbon | ppm |
|---|---|
| 2 | 171.3 |
| 3 | 73.7 |
| 4 | 73.7 |
| 5 | 38.9 |
| 6 | 34.4 |
| 1' | 137.6 |
| 1'' | 139.7 |
| aromatic carbon | 125.1-127.4 |

Derivative of compound of Example 3 (so-called compound 7)

(i) Compound 7i

Compound 7 was acetylated with acetic anhydride to give white syrup. The spectrometric data indicated the compound is the acetate of compound 7.

IR $\gamma_{max}^{film}$ cm$^{-1}$: 3340(N—H), 1760, 1235(ester C=O), 1680(amide C=O), 3080, 3040, 1610, 1500 (monosubstituted benzene).

MS m/z(%): 369(M+, 0.5), 309(M-60, 0.8), 267(309-42, 3) 249(309-60 or 267-H$_2$O, 20), 250(249-1, 53), 179(20), 148(18), 120(30), 105(35), 104(40), 91(38), 77(18), 43(100).

$^1$H-NMR in CDCl$_3$; chemical shift and assignment:

| δ ppm (J, Hz) | H |
|---|---|
| 2.02(s, 3H) | CH$_3$COO |
| 2.05(s, 3H) | CH$_3$COO |
| 2.59(m, 2H) | C$_6$—H |
| 3.39(m, 2H) | C$_5$—H |
| 5.65(d, J=4, 1H) | C$_3$—H |
| 5.88(br, 1H) | N—H |
| 6.30(d, J=4, 1H) | C$_4$—H |
| 6.89-7.08(m, 2H) | |
| 7.15-7.50(m, 8H) | aromatic H |

(ii) Compound 7ii (ketal)

Compound 7 was treated with acetone using hyperchloric acid as catalyst in room temperature to give transparent syrup compound 7ii.

MS m/z(%); 325(M+, 10), 267(40), 177(15), 148(14), 120(100), 119(80), 105(55), 91(75), 77(30).

$^1$H-NMR in CDCl$_3$; chemical shift and assignment:

| δ ppm (J, Hz) | H |
|---|---|
| 1.50 (s, 3H) | CH₃—C |
| 1.65 (s, 3H) | CH₃—C |
| 2.49 (t, J=7, 2H) | C₆—H |
| 3.20 (m, 2H) | C₅—H |
| 4.85 (d, J=7, 1H) | C₃—H |
| 5.48 (d, J=7, 1H) | C₄—H |
| 6.35 (br, 1H) | N—H |
| 7.08–7.50 (m, 10H) | aromatic H |

We claim:

1. A compound of the formula

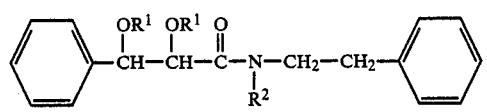

wherein

R¹ representd hydrogen, acetyl or the radicals R¹ taken together form the group and

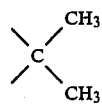

R² represents hydrogen or a methyl group.

2. A compound according to claim 1, wherein R¹ represents hydrogen or acetyl and R² represents hydrogen or a methyl group.

3. A compound according to claim 1, wherein R¹ represents hydrogen and R² represents methyl of the formula

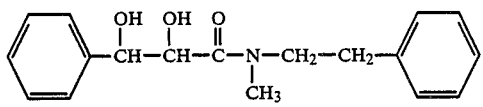

4. A method according to claim 1, wherein R¹ and R² both represents hydrogen of the formula

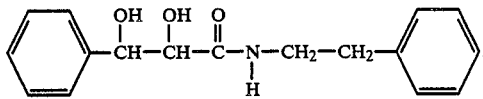

5. A pharmaceutical composition useful in the treatment of hypoxia comprising an amount effective therefor of a compound according to claim 1 and a pharmaceutically acceptable diluent.

6. A method of treating acute or chronic viral hepatitis or liver intoxication comprising administering to a patient in need of such treatment an effective amount of a compound according to claim 1.

7. A pharmaceutical composition useful in the treatment of amnesia comprising an amount effective therefor of a compound according to claim 1 and a pharmaceutically acceptable diluent.

8. A pharmaceutical composition useful as a hepatoprotective agent comprising an amount effective therefor of a compound according to claim 1 and a pharmaceutically acceptable diluent.

9. A method of treating hypoxia comprising administering to a patient in need of such treatment an effective amount of a compound according to claim 1.

10. A method of treating amnesia comprising administering to a patient in need of such treatment an effective amount of a compound according to claim 1.

* * * * *